United States Patent [19]

Posner

[11] Patent Number: 5,738,859
[45] Date of Patent: Apr. 14, 1998

[54] COSMETIC COMPOSITION

[75] Inventor: Robert M. Posner, Merrick, N.Y.

[73] Assignee: Abbe Cosmetic Group International, Inc., Farmingdale, N.Y.

[21] Appl. No.: 783,947

[22] Filed: Jan. 17, 1997

[51] Int. Cl.$^6$ .................................................. A61K 7/00
[52] U.S. Cl. ........................................ 424/401; 514/844
[58] Field of Search .................. 424/401; 514/844, 514/848

[56] References Cited

U.S. PATENT DOCUMENTS 5,476,661  12/1995  Pillai ..................................... 426/401

*Primary Examiner*—Gollamudi S. Kishore
*Attorney, Agent, or Firm*—Jordan and Hamburg

[57] ABSTRACT

A composition for topical application to the skin contains as an essential component at least one of various lipids analogous to those normally found in epidermal skin, including ceramides, sphingolipids (sulfatides, sphingomyelin), phospholipids and cholesterol. In addition to these lipids, other active components act in concert to improve the skin by controlling transepidermal water loss and reversing some of the effects of the aging process. These components, which include combinations of squalane, vitamins A, C, and E, beta carotene, and various oils including evening primrose, avocado, and chamomile, are carried in a base comprised of a suitable silicone or combination thereof, the silicones in a proportion advantageously sufficient to impart a non-oily feel following application. These components act only on the epidermis, almost entirely on the stratum corneum.

19 Claims, No Drawings

COSMETIC COMPOSITION

BACKGROUND OF THE INVENTION

The present invention relates to a cosmetic composition for topical application to skin, and more particularly a cosmetic composition which is effective in improving the quality of skin by intercooperation of active components that together create a moisture barrier against transepidermal water loss, reduce free radicals which are a primary cause of premature aging, and which impart softness and a discernable, desirable, non-oily feel to the skin.

The correct balance of moisture within the skin's stratum corneum is regulated and maintained by biochemical mechanisms involving the interaction and structural organization of specific classes of chemicals naturally occurring in the skin. Known generally as lipids, and including ceramides, sphingolipids (sulfatides, sphingomyelin), phospholipids and cholesterol, these constituents are normally produced by healthy skin, and migrate to the stratum corneum where they form a highly organized structure, functioning at the molecular level to regulate the transepidermal exchange of moisture. As a result of the aging process or damage from environmental factors, such as washing, stress or excessive UV exposure, the presence and/or effectiveness of these lipids may be compromised, resulting in excessive moisture loss. Consequently, the skin's health and vitality is diminished, and fine lines and wrinkles may appear.

In addition to the structural lipids mentioned above, other components present in the skin further contribute to moisture regulation and improved skin texture and water barrier functions. Squalane, for example, enhances skin respiration and inhibits moisture loss.

It has been suggested that replenishment of these lipids and other structural compounds important to transepidermal moisture regulation can be accomplished by topical application of a composition containing a lipid complex. Lipids used in formulating such composition may be derived, for example, utilizing biofermentation techniques, and are then incorporated into a suitable carrier (base) for direct application to the skin.

Although a variety of such lipid preparations have been developed, and are intended for topical application, they have heretofore, as a consequence of the lipid constituency, generally imparted an unappealing oily feel following application and additionally have failed to adequately address the need to incorporate other components important to maintain and replenish the skin to impart youthful appearance. A composition comprising a suitable base for delivery of the structural hydrophobic lipids to the skin which would limit this oily after-feel and impart youthful skin appearance and texture, as well as reversing some of the effects of environmental damage and aging, by virtue of additional interacting active ingredients, would be therefore highly desirable.

SUMMARY OF THE INVENTION

Accordingly, it is an object of the invention to provide a composition for topical application which delivers hydrophobic lipids and other active components to the skin for regulation of transepidermal water loss and improvement in overall skin quality which overcomes the drawbacks in the prior art.

It is a further object to provide a topically applied composition which includes a complex of active ingredients compounded in a base which avoids an oily after-feel following application to the skin.

Yet another object of the invention is to provide a topically applied composition which contains a variety of components which work together to reduce moisture loss, increase skin respiration, at least partially eliminate free radicals, and modify the ratio of soluble to insoluble collagen for the appearance and feel of more youthful skin.

Briefly stated, the invention is directed to a composition for topical application to the skin which contains as an essential component at least one of various lipids analogous to those normally found in epidermal and dermal skin, including ceramides, sphingolipids (sulfatides, sphingomyelin), phospholipids and cholesterol. In addition to these lipids, other active components act in concert to improve the skin by controlling transepidermal water loss and reversing some of the effects of the aging process. These components, which include combinations of squalane, vitamins A, C, and E, beta carotene, and various oils including evening primrose, avocado, and chamomile, are carried in a base comprised of a suitable silicone or combination thereof, the silicones in a proportion advantageously sufficient to impart a non-oily feel following application. Suitable silicones include, for example, cyclomethicone, dimethiconol, phenyl trimethicone, hexamethyldisiloxane, etc, which, as it was found quite unexpectedly by experimentation, in a critical range impart a dry, powdery, satin feel when a complex containing a sufficiently high percentage of the selected silicones is applied.

An embodiment in accordance with the invention incorporates in the composition, silicone in a preferred range from about 70% to about 90%, lipid/silicone complex in a preferred range from about 5% to about 25%. Other optional enhancing components make up the preferred balance of 5% or less.

The above and other objects, features and advantages of the invention will become readily apparent from the following detailed description thereof.

DETAILED DESCRIPTION OF THE INVENTION

The composition in accordance with an embodiment of the invention is comprised of any of various lipids structurally akin to those found normally in dermal and epidermal skin, and which are possessed of the same hydrophobic properties. Ideally, these include, for example, various ceramides, sphingolipids (sulfatides, sphingomyelin), phospholipids and cholesterol, and are advantageously used in combination to more closely mimic the body-produced structural lipids which they are intended to supplement following topical application. Because of ethical, allergenic or other concerns over animal derived lipids, the invention advantageously incorporates lipids obtained by known biofermentation techniques. Lipids suitable for use in carrying out the invention are conveniently available as a hydrophobic sphingolipid complex (HSC) from CENTERCHEM, INC., 225 High Ridge Road, Stamford, Conn. 06905, which product contains a proprietarily derived combination of ceramides, sphingolipids, and cholesterol in a silicone/emollient matrix, and which is free of surfactants which, it is noted, would diminish the effectiveness of the composition prepared in accordance with the embodiment of the invention. The lipids, however, may also be obtained from alternate sources in their unblended state and mixed as desired to achieve the goals of the invention as claimed herein, provided ranges for the lipids are adjusted to account for the already diluted concentrations in the HSC.

The above obtained lipids are incorporated in a base comprised of a suitable silicone or combination of silicones which serve as a carrier. Silicones suitable for use include, for example, cyclomethicone, dimethiconol, phenyl trimethicone, hexamethyldisiloxane, etc., which, as it was found quite unexpectedly by experimentation, when used in critical ranges, impart a dry, powdery, satin feel when a complex containing a sufficiently high percentage of the selected silicones are applied. Suitability of particular silicone or mixture thereof is based upon property considerations, including viscosity and volatility which ultimately influence the feel of the applied composition, and permit the absorption of the lipids at a desired rate by permitting an adequate volatilization rate, for the desired satiny, dry sensation, rather than oily. Examples of silicones which have been found by experimentation to achieve the desired results as set forth herein are available from Dow Corning, and include silicones numerically designated as 344 (cyclomethicone), 245 (cyclomethicone), 244 (cyclomethicone), 1401 (mixture of cyclomethicone and dimethiconol), 1404 (mixture of cyclomethicone and dimethiconol) and 200 (0.65 cSt viscosity Hexamethyldisiloxane). Other silicones possessing similar properties and available from other sources will also serve as an effective base in carrying out the invention within the scope as claimed. It is noted that Dow Corning 1401 fluid and 344 fluid (or silicones having equivalent properties) are preferred as the silicone base, and more preferably a combination of the two.

The composition further comprises other active ingredients which, by acting in concert with each other, as well as the lipid constituents, provide the many skin benefits provided by the invention as claimed, limiting moisture loss and providing improvement in skin quality. These components include various combinations of squalane, vitamins A, C, and E, beta carotene, and various oils including evening primrose, avocado, and chamomile. Each functions in a particular cooperational manner with the other components to provide benefits in preserving and restoring skin plumpness and suppleness, at least partially eliminating free radicals, and aiding in restoring the moisture barrier in the stratum corneum, the benefits associated with each component being addressed in detail below. It is importantly noted that by virtue of the unique combination of components, the composition requires no added preservatives.

Squalane, a substance normally found in the epidermal layer of the skin, is non-irritating, non-sensitive and hypo-allergenic. Its emollient activity imparts softness to the skin without leaving an oily after-feel, and increases skin respiration and acts to prevent moisture loss in conjunction with the lipids. Squalene has been shown to increase the rate of penetration of other compounds into the skin, and its use in the invention therefore facilitates the delivery of the other active components comprising the topically applied composition. It also is believed to increase the physiological activity of other substances. In addition, squalene is highly stable, resisting oxidation and degradation, even when exposed to extremes of temperatures, contributing to the shelf life of the overall composition.

Vitamin A (retinyl palmitate), another advantageous component, is readily absorbed by the skin, where it functions as a skin "normalizer", enabling the skin to remain soft and plump, and also as an anti-keratinizing agent. In addition, it further limits transepidermal water loss, as does vitamin E (acetate or linoleate), another advantageous component.

Vitamins E, C and beta carotene act as anti-oxidants, engulfing and destroying free oxygen singlets (free radicals) in and on the skin, and function to curtail some of the effects of premature aging otherwise caused thereby.

A variety of plant oils are also advantageously included in the composition in accordance with the invention, and provide various cooperative benefits when used in combination with the aforementioned constituents. Avocado oil, for example, derived from avocado lipids, may be used as a skin conditioning moisturizer and emollient, to impart additional moisture content to the skin. Additionally, studies have shown that avocado unsaponifiables can modify the ratio of soluble to insoluble collagen, a process which is the reverse of what happens as the result of aging. Avocado oil also has the effect of soothing sensitive skin and alleviating minor skin conditions.

Another advantageously included plant oil component is evening primrose oil, a widely known source of gamma-linolenic acid (GLA). GLA is one of the essential fatty acids vital to the maintenance of normal epithelial barrier membrane function. Such essential fatty acids are also known to reduce transepidermal water loss.

Chamomile oil is also a useful optional component, providing a soothing and calming influence on the skin.

An embodiment in accordance with the invention incorporates in the composition, silicone in a preferred range of about 70% to about 90%, and lipids (contained in and added to the mixture as HSC) in a preferred range of about 5% to about 25%. It is noted that if lipids are obtained in their unblended form rather than as a lipid/silicon matrix, a lower percentage may be acceptable (for example about 0.1% to about 12%), and required, to achieve an equivalent product, insofar as lipids comprise only a portion of the composition of the HSC product. Other active components, used in various combinations, including, for example, squalane, vitamins A, C, and E, beta carotene, and various oils including evening primrose, avocado, and chamomile, make up the preferred balance of less than 5%. All percentages herein are by weight.

The preferred ranges for the various components in the various possible combinations are as follows: vitamins A, C and E are each in a range of about 0.2% to about 1%, squalene is in a range of about 0.2% to about 1%, avocado oil is in a range of about 0.01% to about 0.2%, evening primrose oil is in a range of about 0.01% to about 0.2%, chamomile oil in a range of about 0.01% to about 0.2%, and beta carotene is in a range of about 0.01% to about 0.1%.

In an advantageous embodiment, a composition is comprised of HSC, silicone, vitamin E (tocopherol acetate), squalane, and avocado oil. Preferably, Dow Corning 1401 fluid and 344 fluid are used together as the silicone base, the former in a preferred range of about 35% to about 58%, and the latter in a range of about 25% to about 45%. HSC is added in a range of about 8% to about 20%. Vitamin E is present in a preferred range of about 0.2% to about 1%. Squalene is in a preferred range of about 0.2% to about 1%. The preferred range for the avocado oil is about 0.01% to about 0.2%.

In a particularly advantageous embodiment, a composition is comprised of HSC, silicone, vitamin E (tocopherol acetate), vitamin A, squalane, evening primrose oil and avocado oil. Dow Corning 1401 fluid and 344 fluid are used together as the silicone base, the former in a preferred range of about 35% to about 58%, and the latter in a range of about 25% to about 45%. HSC is added in a range of about 8% to about 20%. Vitamin E is present in a preferred range of about 0.2% to about 1%, as is vitamin A. Squalene is in a preferred range of about 0.2% to about 1%. The preferred range for the evening primrose oil is about 0.01% to about 0.2%, as is avocado oil.

The invention will now be described further with reference to the following examples, considered illustrative of various embodiments. It will be understood that they are in no way intended to restrict the invention disclosed herein, but rather to extend the scope of the foregoing disclosure and the claims which follow.

EXAMPLES

In an example of a method to produce the composition in accordance with an embodiment of the present invention, the components of the composition are weighed separately and then mixed together. The product composition is manufactured cold. The various ingredients are added consecutively in order of weight, preferably beginning with the silicone, for example, in the above described embodiment, with Dow Corning 1401. The composition is then mixed thoroughly to assure homogeneity.

Example 1

An example of the composition produced by the above method includes 49.95% Dow Corning 1401 fluid, 37% Dow Corning 344 fluid, 11.95% Hydrophobic Sphingolipids Complex, 0.4% vitamin E (tocopherol acetate), 0.4% squalane, 0.1% vitamin A, 0.1% avocado oil, and 0.1% primrose oil. All percentages are by weight.

The composition thus formed is applied to the skin. At first the product has an oily feel, but as the silicones volatilize, this changes to a dry, powdery, satin feel. This unique and desirable aspect was discovered quite unexpectedly, and is thought to be attributed to the major proportion of silicone used in the carrier in the critical ranges disclosed, in contrast with prior art topical preparations using lipids in a carrier which typically provides a somewhat oily after-feel.

The result of topical application is an improvement in skin softness and plumpness by virtue at least in part of a reduction of transepidermal water loss, an increase in skin respiration, an upward modification of the ratio of soluble to insoluble collagen, which normally decreases due to the aging process, and at least partial protection against free radicals, all of which contribute to reduce the negative effects of the environment and the aging process on the skin.

Example 2

An amount of beta carotene is added to the prepared composition of Example 1 in an amount representing up to about 0.2% of the total by weight. Because beta carotene is a potent antioxidant, when applied to the skin, the modified composition provides additional protection against free radicals.

Example 3

The composition of Example 1 is prepared, substituting, in like quantities, vitamin C in place of vitamin A. Vitamin C imparts additional antioxidant properties to the overall modified composition.

Example 4

The composition of Example 1 is prepared, substituting, in like quantities, chamomile oil in place of evening primrose oil, giving the product an additional soothing, calming quality.

Example 5

An example of another composition produced by the above method includes 49.95% Dow Corning 1401 fluid, 37% Dow Corning 344 fluid, 12.2% Hydrophobic Sphingolipid Complex, 0.4% vitamin E (tocopherol acetate), 0.4% squalene, 0.05% beta carotene. All percentages are by weight.

The benefits are similar to those of the aforementioned examples, with increased antioxidant potential.

Having described the present invention, it should be appreciated that the present invention is not limited to the examples described, in that various changes and modifications can be effected therein by one of ordinary skill in the art without departing from the scope of the invention as defined by the appended claims.

I claim:

1. A composition for topical application to the skin, comprising silicone in a range of about 70% to about 90%, hydrophobic sphingolipid complex of a combination of ceramides, sphingolipids, and cholesterol in a silicone/emollient matrix, said hydrophobic sphingolipid complex being present in a range of about 5% to about 25%, and at least one component selected from the group consisting of squalane, vitamin A, vitamin C, vitamin E, beta carotene, evening primrose oil, avocado oil, and chamomile oil in a range up to 5%.

2. The composition of claim 1, wherein said silicone is a combination of cycomethicone and a mixture of cyclomethicone and dimethiconol.

3. The composition of claim 1, wherein said component is vitamin E, squalane, and beta carotene.

4. The composition of claim 2 wherein, when present, the vitamins A, C and E are each in a range of about 0.2% to about 1%, the squalane is in a range of about 0.2% to about 1%, the avocado oil is in a range of about 0.01% to about 0.2%, the evening primrose oil is in a range of about 0.01% to about 0.2%, the chamomile oil is in a range of about 0.01% to about 0.2%, and the beta carotene is in a range of about 0.01% to about 0.1%.

5. The composition of claim 2, wherein the mixture of cyclomethicone and dimethiconol is present in a range of about 35% to about 58% and the cyclomethicone is present in a range of about 25% to about 45%.

6. The composition of claim 4, wherein the hydrophobic sphingolipid complex is in a range of about 8% to about 20%.

7. The composition of claim 5, wherein the hydrophobic sphingolipid complex is in a range of about 8% to about 20%, and the component is vitamin E in a range of about 0.2% to about 1%, squalane in a range of about 0.2% to about 1%, and beta carotene in a range of about 0.01% to about 0.1%.

8. The composition of claim 5, wherein the mixture of cyclomethicone and dimethiconol is present in an amount of about 49.95%, the cyclomethicone is in an amount of about 37%, the hydrophobic sphingolipid complex is in an amount of about 12.2%, and the component is vitamin E in an amount of about 0.4%, squalane in an amount of about 0.4%, and beta carotene in an amount of about 0.05%.

9. A composition for topical application to the skin, comprising silicone in a range of about 70% to about 90%, hydrophobic sphingolipid complex of a combination of ceramides, sphingolipids, and cholesterol in a silicone/emollient matrix, said hydrophobic sphingolipid complex being present in a range of about 8% to about 20%, vitamin E in a range of about 0.2% to about 1%, squalane in a range of about 0.2% to about 1%, vitamin A in a range of about 0.2% to about 1%, avocado oil in a range of about 0.01% to about 0.2%, and primrose oil in a range of about 0.01% to about 0.2%.

10. The composition of claim 9 wherein the silicone is a combination of cycomethicone and a mixture of cyclomethicone and dimethiconol.

11. The composition of claim 10 wherein the mixture of cylomethicone and dimethiconol is present in a range of about 35% to about 58% and the cyclomethicone is present in a range of about 25% to about 45%.

12. A composition for topical application to the skin, comprising silicone in a range of about 83% to about 99%, a mixture of ceramides, sphingolipids, phospholipids and cholesterol in a range of about 0.1% to about 12%, and at least one component selected from the group consisting of squalane, vitamin A, vitamin C, vitamin E, beta carotene, evening primrose oil, avocado oil, and chamomile oil in a range up 5%.

13. The composition of claim 6 wherein said silicone is a combination of cyclomethicone and a mixture of cyclomethicone and dimethiconol.

14. The composition of claim 12 wherein, when present, the vitamins A, C and E are each in a range of about 0.2% to about 1%, the squalane is in a range of about 0.2% to about 1%, the avocado oil is in a range of about 0.01% to about 0.2%, the evening primrose oil is in a range of about 0.01% to about 0.2%, the chamomile oil in a range of about 0.01% to about 0.2%, and the beta carotene is in a range of about 0.01% to about 0.1%.

15. The composition of claim 13 wherein the mixture of cyclomethicone and dimethiconol is present in a range of about 35% to about 58% and the cyclomethicone is present in a range of about 25% to about 45%.

16. The composition of claim 12 wherein said silicone is a combination of a mixture of cyclomethicone and dimethiconol present in a range of about 35% to about 58% and cyclomethicone present in a range of about 25% to about 45%.

17. The composition of claim 16 wherein said component is vitamin E present in a range of about 0.2% to about 1%, squalane present in a range of about 0.2% to about 1%, vitamin A present in a range of about 0.2% to about 1%, avocado oil present in range of about 0.1% to about 0.2% and evening primrose oil present in a range of about 0.1% to about 0.2%.

18. The composition of claim 7, wherein the component further comprises at least one oil in a range of about 0.1% to about 0.2%, the oil being selected from the group consisting of evening primrose, avocado and chamomile.

19. The composition of claim 8, wherein the component further comprises at least one oil in a range of about 0.1% to about 0.2%, the oil being selected from the group consisting of evening primrose, avocado and chamomile.

* * * * *

UNITED STATES PATENT AND TRADEMARK OFFICE
CERTIFICATE OF CORRECTION

PATENT NO. : 5,738,859
DATED : April 14, 1998
INVENTOR(S) : Robert M. Posner

It is certified that error appears in the above-indentified patent and that said Letters Patent is hereby corrected as shown below:

Column 3, line 48, change "Squalene" to --Squalane--; and
         line 53, change "squalene" to --squalane--.

Column 4, line 53, change "Squalene" to --Squalane--; and
         line 64, change "Squalene" to --Squalane--.

Column 6, line 3, change "squalene to --squalane--.

Signed and Sealed this

FourthDay of August, 1998

Attest:

BRUCE LEHMAN

Attesting Officer     Commissioner of Patents and Trademarks